(12) United States Patent
Matacotta et al.

(10) Patent No.: US 6,781,019 B2
(45) Date of Patent: Aug. 24, 2004

(54) METHOD FOR ABSORBING FORMALDEHYDE FROM GASEOUS MIXTURES THAT CONTAIN IT

(75) Inventors: Francesco Cino Matacotta, Trieste (IT); Petr Nozar, Bologna (IT); Chiara Dionigi, Perugia (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 0 days.

(21) Appl. No.: 10/335,023

(22) Filed: Dec. 31, 2002

(65) Prior Publication Data

US 2004/0127751 A1 Jul. 1, 2004

(51) Int. Cl.[7] .................................................. C07C 45/78

(52) U.S. Cl. ........................ 568/491; 568/493; 568/562
(58) Field of Search ................................. 568/491, 493, 568/562

(56) References Cited

U.S. PATENT DOCUMENTS 6,358,374 B1 * 3/2002 Obee et al. .............. 204/157.3

* cited by examiner

Primary Examiner—Johann Richter
Assistant Examiner—Sikarl A. Witherspoon
(74) Attorney, Agent, or Firm—Wood, Phillips, Katz, Clark & Mortimer

(57) ABSTRACT

A method for absorbing formaldehyde from gaseous mixtures that contain it, and a method for regenerating the absorption compound used.

15 Claims, 10 Drawing Sheets

LEGEND

1. FURNACE (25°C < T < 200°C)
2. CRUCIBLE WITH PARAFORMALDEHYDE
3. HEATING BELT (250°C)
4. ABSORPTION MATERIAL
5. TRAPS WITH WATER

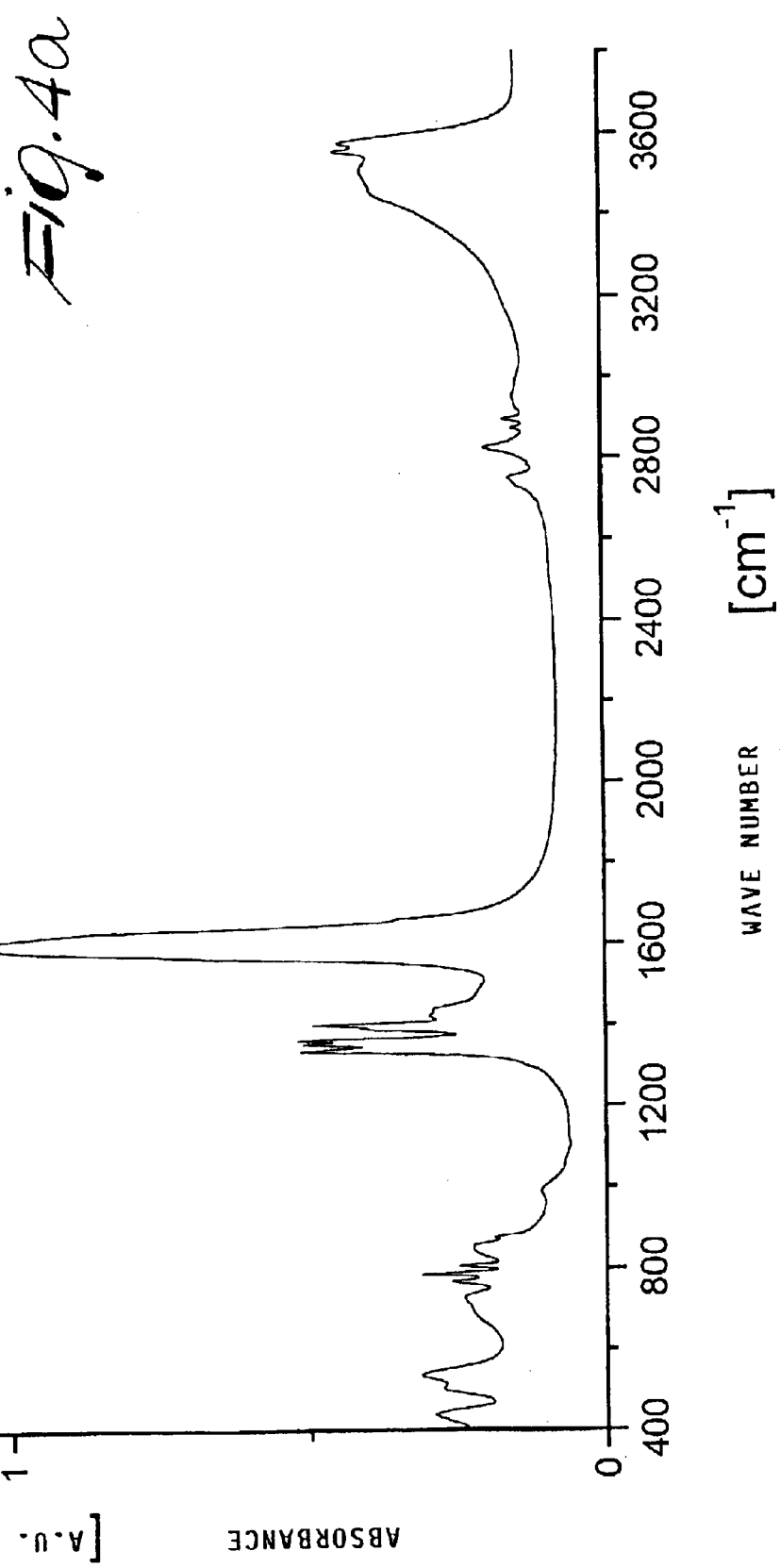

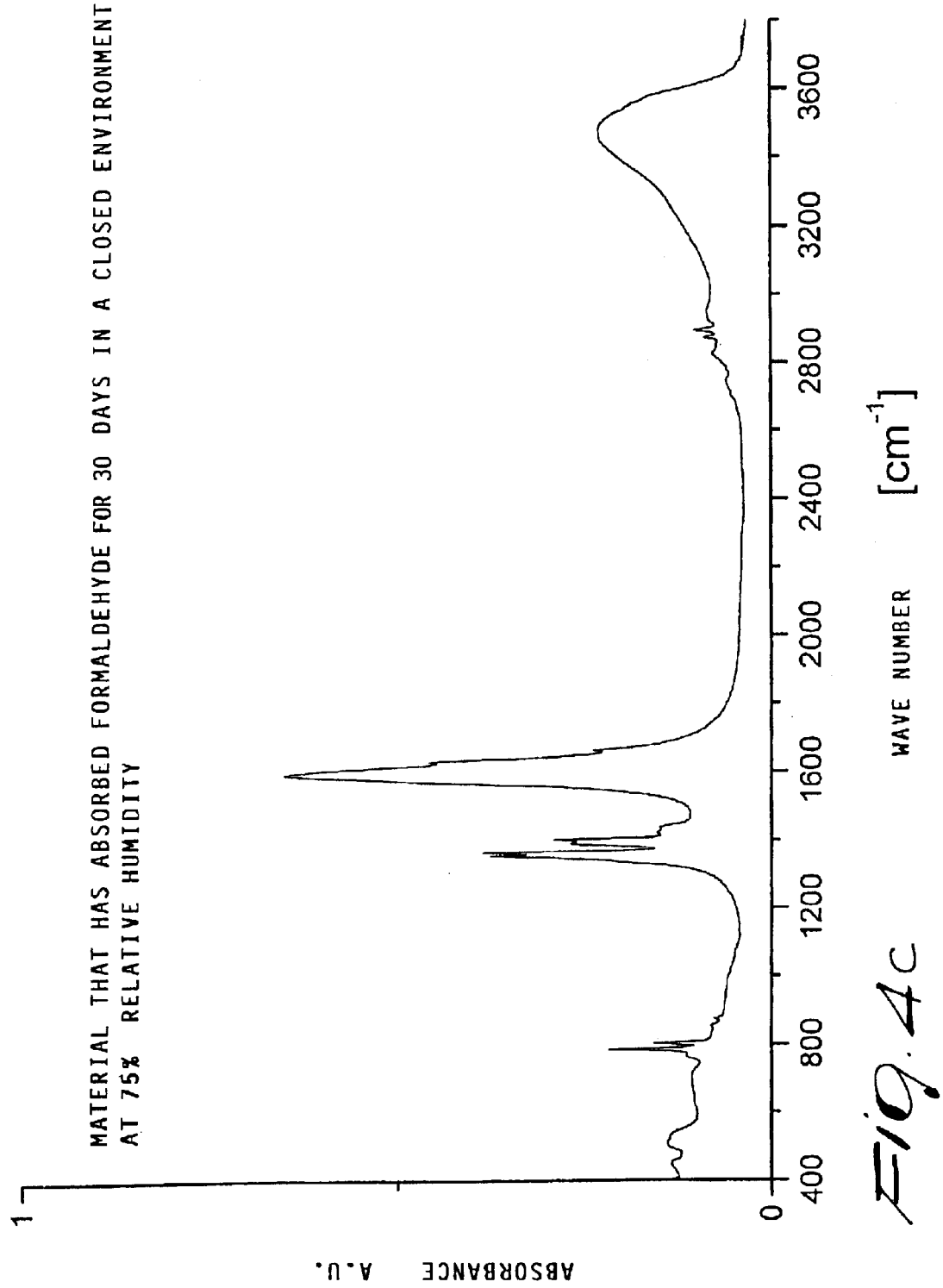

METHOD FOR ABSORBING FORMALDEHYDE FROM GASEOUS MIXTURES THAT CONTAIN IT

BACKGROUND OF THE INVENTION

The present invention relates to a method for absorbing formaldehyde from gaseous mixtures that contain it and to a method for regenerating the absorption compound used.

A study conducted by the EPA (Environmental Protection Agency) of the United States and lasting over 10 years has shown that some atmospheric pollutants concentrate more in enclosed environments than outdoors, with a negative effect on our state of health.

In particular, it has been observed that building materials and furniture can release toxic chemicals for long periods of time.

Formaldehyde ($H_2C=O$) is the most important of the gases that pollute indoor environments and is a component of the atmosphere that forms as a stable intermediate in the oxidation of methane or other volatile organic compounds. While its outdoor concentration is generally too low to be important (approximately 0.01 ppm in built-up areas, except in episodes of photochemical smog), the indoor level of formaldehyde is often greater by orders of magnitude (on average 0.1 ppm, but sometimes >1 ppm).

The main sources of emission of this gas in homes are cigarette smoke and the synthetic resins and foams based on urea-formaldehyde used as insulating materials. These resins and foams, in certain conditions such as high humidity, both release high rates of formaldehyde for long periods of time.

One of the main uses of formaldehyde is in the production of synthetic resins. These synthetic resins, such as urea-formaldehyde, melamine-formaldehyde, urea-melamine-formaldehyde, phenol-resorcinol-formaldehyde, have long been used as adhesives in the wood industry to produce panels of particleboard and plywood. The resins are capable of releasing formaldehyde for long periods of time.

Although formaldehyde has been used in the past mainly as disinfectant for sanitary environments, clothes, garments and utensils of sick individuals, it is a substance that in addition to being a known allergen is a suspected mutagen and carcinogen for human beings (information in this regard is provided in the circular letter dated 22 Jun. 1983, no. 57, of the Ministry of Health, entitled "Usi della formaldeide, rischi connessi alle possibili modalità di impiego" [Uses of formaldehyde, risks linked to its possible methods of use].

To avoid damage to health, a series of European standards (EN 120, EN 717-2, EN 717-1) is currently in force and lists "the directives for use of particleboard panels in enclosed spaces", which set the maximum allowed limits for release of formaldehyde (Table 1).

TABLE 1

| Material | Class | EN 120 mg HCOH/100 mg | EN 717-2 mg HCOH/$m^2$h | | EN 717-1 ppm |
|---|---|---|---|---|---|
| Raw particleboard | E1 | ≦6.5  ≦8.0 | Average value | Individual value | 0.1 |
| Raw fiberboard | E1 | ≦7.0  ≦8.0 | | | 0.1 |
| Veneered plywoods | E1 | | Within 3 days ≦5.0 | ≦6.0 | 0.1 |
| | | | After 4 weeks ≦2.5 | ≦3.5 | 0.1 |
| Laminated particleboard and fiber board | E1 | | ≦2.5 | ≦3.5 | 0.1 |
| Laminated plywoods | | | ≦2.5 | ≦3.5 | 0.1 |
| Particleboard and fiberboard intended for lamination | E1B | ≦10.0 | | | |
| Particleboard for cladding, reverse side cladding or facing | E2, E3 | | | | 0.1–1.0 1.0–2.3 |

The methods for eliminating formaldehyde cited in patent literature mainly relate to solutions of functionalized phenols to be used in a mixture with the formaldehyde-containing synthetic resins and capable of absorbing the released formaldehyde. Information is also provided on formaldehyde-absorbing materials, supported by porous silicates and characterized by active functional groups such as amines, thiols and sulfonic acid, JP 11228954A.

These methods for eliminating formaldehyde lead to products in which the formaldehyde is bonded chemically to the absorber in a manner similar to what occurs between formaldehyde and the other monomers used for the resins. The elimination of the formaldehyde trapped by the absorber is possible only by combustion of the formaldehyde-absorber system and with environmental consequences that are similar to those encountered in the combustion of said resins. The present invention provides an alternative way of trapping the formaldehyde within a matrix constituted by inorganic material and for converting the formaldehyde into environmentally compatible products by virtue of low-temperature (>200° C.) thermal treatments.

SUMMARY OF THE INVENTION

The aim of the present invention is to eliminate the drawbacks noted above of known methods for eliminating formaldehyde from gaseous mixtures that contain it, which allows to eliminate the formaldehyde and to further convert completely the formaldehyde into fully environmentally compatible products.

An object of the present invention is to provide a method for absorbing formaldehyde that has a low cost.

Another object of the present invention is to provide a method for absorbing formaldehyde that uses a regenerable absorption agent and a method for regenerating said absorption agent.

This aim and these and other objects are achieved by the method according to the present invention for absorbing formaldehyde from gaseous mixtures that contain it, said method comprising the step of contacting gaseous mixtures that contain formaldehyde with absorption compounds constituted by mixed oxides of copper chosen among $Ca_{4+x}Cu_5O_{10}$, where $0 \leq x \leq 1$, derivatives thereof by isovalent and/or heterovalent substitutions, and mixtures thereof. Preferably, in the method according to the invention absorption occurs in the presence of oxygen and/or water vapor.

DETAILED DESCRIPTION OF THE INVENTION

An absorption compound that is preferred for use in the method according to the invention is $Ca_{4.1}Cu_5O_{10}$.

Other absorption compounds that can be used preferably in the method according to the present invention are derivatives of $Ca_{4+x}Cu_5O_{10}$, where $0 \leq x \leq 1$, by substitution of sites occupied by calcium, preferably with metals of the second group, such as magnesium or strontium, particularly $Ca_{0.85}Mg_{0.15}CuO_2$ and $Ca_{0.85}Sr_{0.15}CuO_2$.

Other absorption compounds preferably usable in the method according to the present invention are derivatives of $Ca_{4+x}Cu_5O_{10}$, where $0 \leq x \leq 1$, by isovalent and heterovalent substitution if the sites are occupied by copper, particularly with fourth-period transition metals such as Ni, such as $CaCu_{0.45}Ni_{0.15}O_2$.

The compounds and their derivatives are known in the literature (Roth et al., J Am Ceram Soc, Vol. 72, p. 1545 (1989)).

In the method according to the present invention, absorption occurs at a temperature between 0 and 150° C., preferably at ambient temperature. In the method according to the invention, the absorption of formaldehyde from gaseous mixtures that contain it can occur in flowing conditions or in static conditions, in a closed environment.

In another aspect, the present invention relates to a method for regenerating the spent absorption compound produced by the method for absorbing formaldehyde from gaseous mixtures that contain it.

The regeneration method according to the present invention comprises the step of heating the spent absorption material to a temperature of approximately 700° C. in a stream of oxygen.

In another aspect, the present invention provides a method for converting the absorbed formaldehyde into non-polluting products, particularly water and carbon dioxide, said method comprising the step of heating the spent absorption material, produced by the method of absorbing formaldehyde of a gaseous mixture that comprises it, to a temperature of more than 200° C., preferably between 200 and 700° C.

The inventors of the present invention have found that the treatment of the spent absorption material at temperatures above 200° C. leads to the oxidation of the spent absorption material produced by the formaldehyde absorption method according to the present invention into a mixture of carbonates and oxides.

The inventors of the present invention have also found that the treatment of the mixture of carbonates and oxides thus obtained at 700° C. in a stream of oxygen leads to regeneration of the absorption material.

Figure 1:
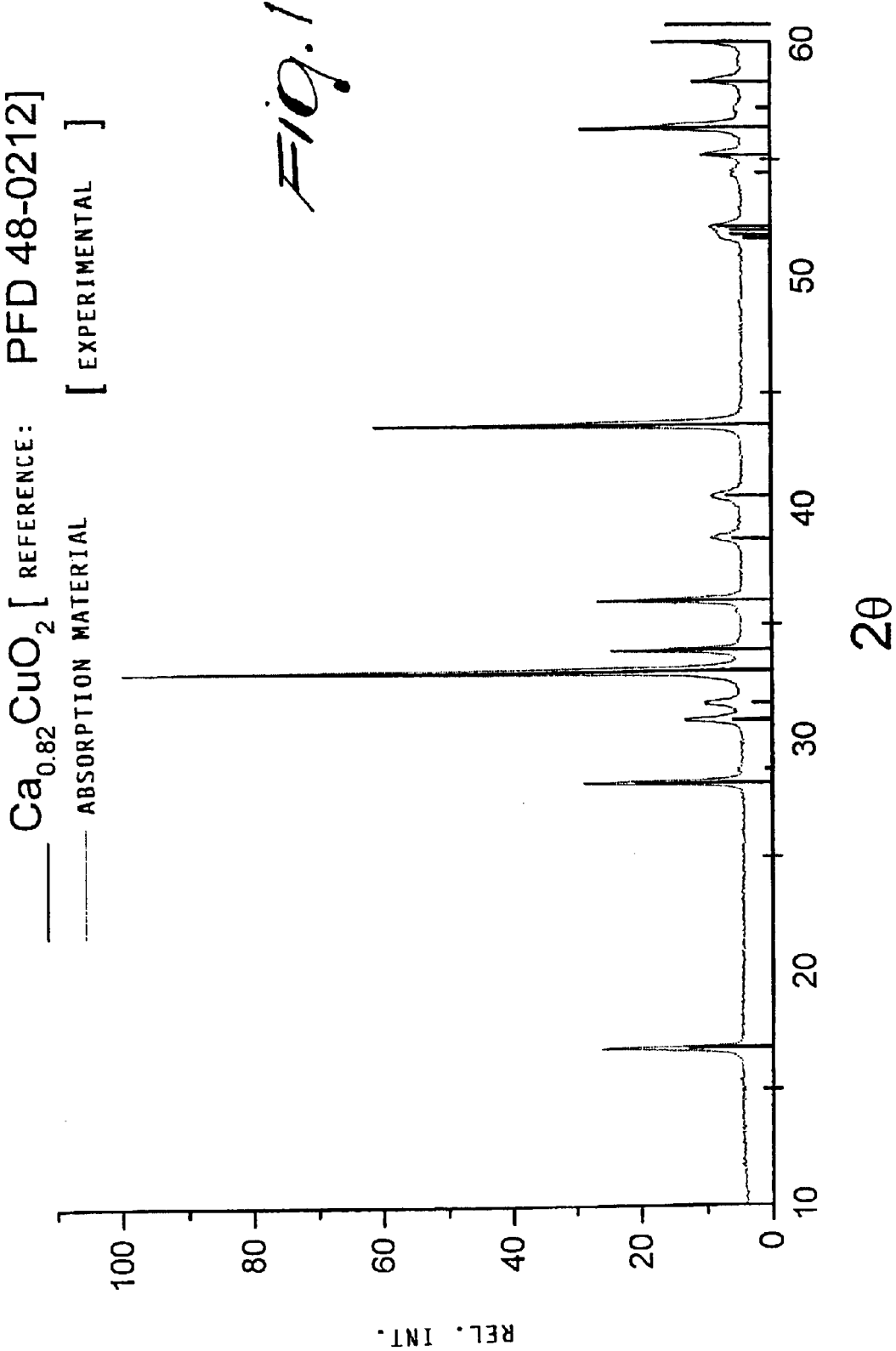
FIG. 1 is the X-ray spectrum of the powder and the diffraction spectrum of the powders of the $Ca_{0.82}CuO_2$ material designed by the code 48-0212 in the PDF database.

To characterize the properties of formaldehyde absorption and regeneration of the absorption compounds used in the method according to the present invention, particularly of the compound of the $Ca_{4.1}Cu_5O_{10}$ type and the regeneration properties of the compound of the $Ca_{4.1}Cu_5O_{10}$ type, two different series of experiments were conducted by using material synthesized by means of methods cited in the documents of the literature in the name of Roth et al. and Siegrist et al. (Roth R S, Rawan C J, Ritter J J, Burton B P, J Am Ceram Soc 1989, 72, 1545; Siegrist T, Roth R S, Rawan C J, Ritter J J, Chemistry of Materials, 1990, 2, 192). The material used is believed to be characterized unequivocally, apart from the chemical formulation, which in this class of Ca—Cu—O compounds can vary over a certain range tolerated by the structure, by the X-ray spectrum of the powder shown in FIG. 1. FIG. 1 also shows, for the sake of comparison, the diffraction spectrum of the powders of the $Ca_{0.82}CuO_2$ material designated by the code 48-0212 in the PDF database.

The examples that follow must be understood as illustrating but not limiting the scope of the present invention.

The two series of experiments conducted are:

A. Experiments of absorption in isothermal conditions, at different relative humidities, in order to characterize the absorption capacity of the materials.
  A1. Absorption in flowing conditions.
  A2. Absorption in a closed environment.
B. Experiments in isothermal conditions, in order to characterize the material regeneration method.

The experiments were conducted by using the following gaseous mixtures:

A.1) Absorption in flowing conditions:

The experiments of absorption in flowing conditions were conducted in humidified synthetic air containing formaldehyde obtained from the thermal breakdown of a polymer (for example paraformaldehyde) capable of releasing formaldehyde.

Paraformaldehyde is a polymer that is sensitive to humidity and absorbs water if stored in natural air. To determine the formaldehyde content in the paraformaldehyde stored in natural air, 200 mg of paraformaldehyde were broken down in water at 60° C. The resulting aqueous solution of formaldehyde was subjected to iodometric titration (by using the procedure given in the UNI EN 717-3 standard for formaldehyde determination) and was found to contain 182 mg of formaldehyde.

In particular, the example of absorption in flowing conditions listed hereafter was conducted in a stream of air (100 ml/min) humidified at 3.5% and containing, for the duration of the experiment, a variable concentration of formaldehyde whose average value is ~0.26% by weight. The gaseous formaldehyde was obtained by breaking down 200 mg of paraformaldehyde to 182 mg of formaldehyde in ~12 hours in the temperature range 25–190° C.

A.2) Absorption in a closed environment:

The experiments of absorption in a closed environment use the atmosphere in equilibrium, at ambient temperature, with a polymer that contains formaldehyde and is capable of releasing it (for example paraformaldehyde, which has a vapor pressure of 1.45 mm Hg) and aqueous solutions. The resulting atmosphere contains formaldehyde (~0.25% by weight) at a relative humidity of 100, 75 and 51%, obtained respectively with the presence in the environment of deionized water and saturated aqueous solutions of NaCl and $Ca(NO_3)$ salts.

B) Regeneration:

The experiments of regeneration of the material were conducted by using dry synthetic air for temperatures lower than 700° C. and an oxygen atmosphere at 700° C.

A.1 Experiments of absorption in flowing conditions

An example of experiment in flowing condition is given. The experiment in flowing conditions was performed by using 1.1 g of $Ca_{4.1}Cu_5O_{10}$ absorption material (0.5–3 mm pellets) supported by ceramic wool and placed at the center of a tubular reactor made of quartz (with a diameter of 1.5 cm), in which the mixture of humid gas containing formaldehyde was made to flow for ~12 hours. During the experiment, the reactor, placed outside the furnace in which the paraformaldehyde is broken down, reached a maximum temperature of 40° C. The reactor was connected to the furnace with a tube made of Pyrex glass. The reactor-furnace connection tube was heated to the temperature of 250° C. to prevent the formaldehyde from polymerizing on the walls of the tube.

Figure 2:
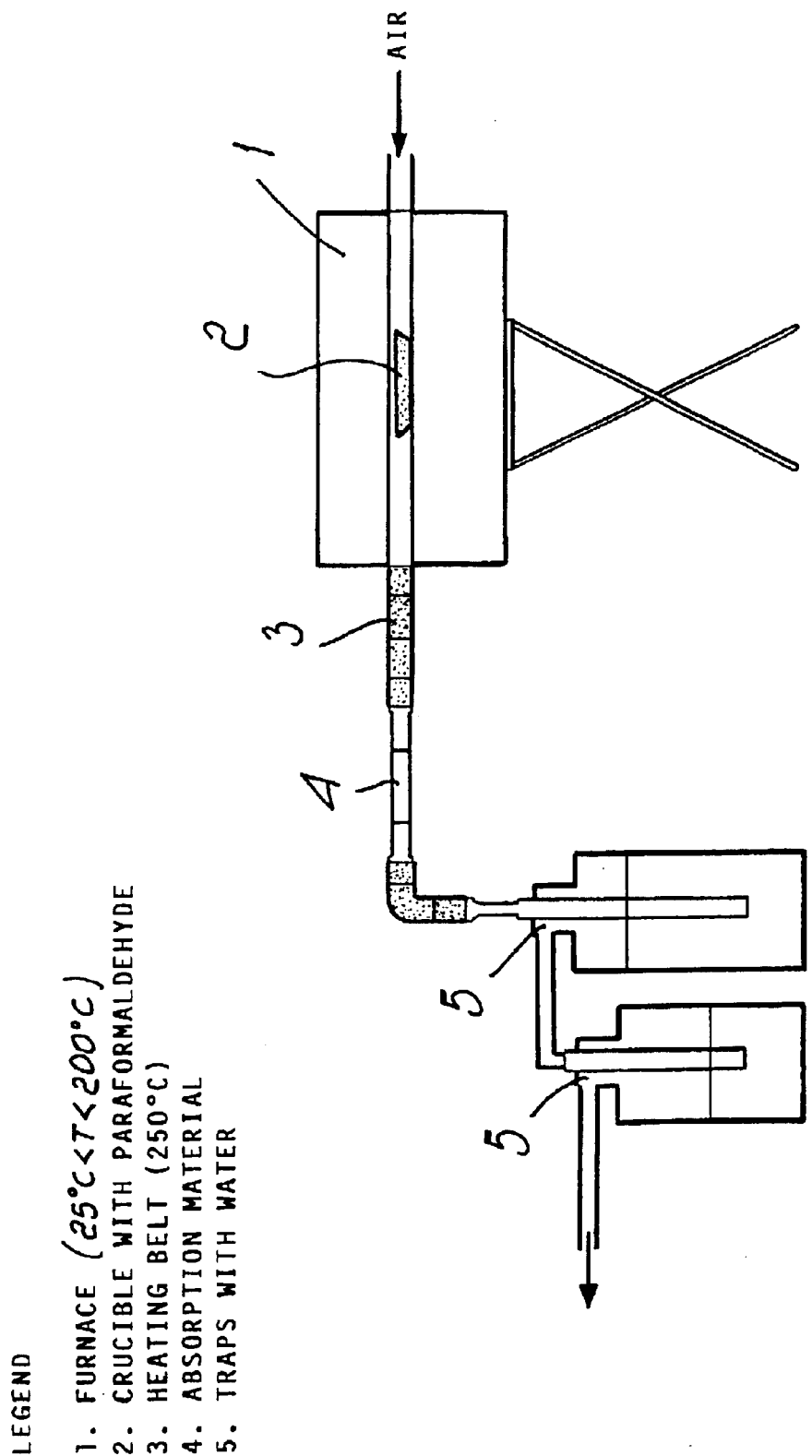
FIG. 2 is the apparatus used for the absorption experiment in flowing conditions.

FIG. 2 shows the apparatus used.

The gas leaving the reactor was bubbled through inside two traps arranged in series, the first one containing 500 ml of water, the second one containing 250 ml.

Figure 3:
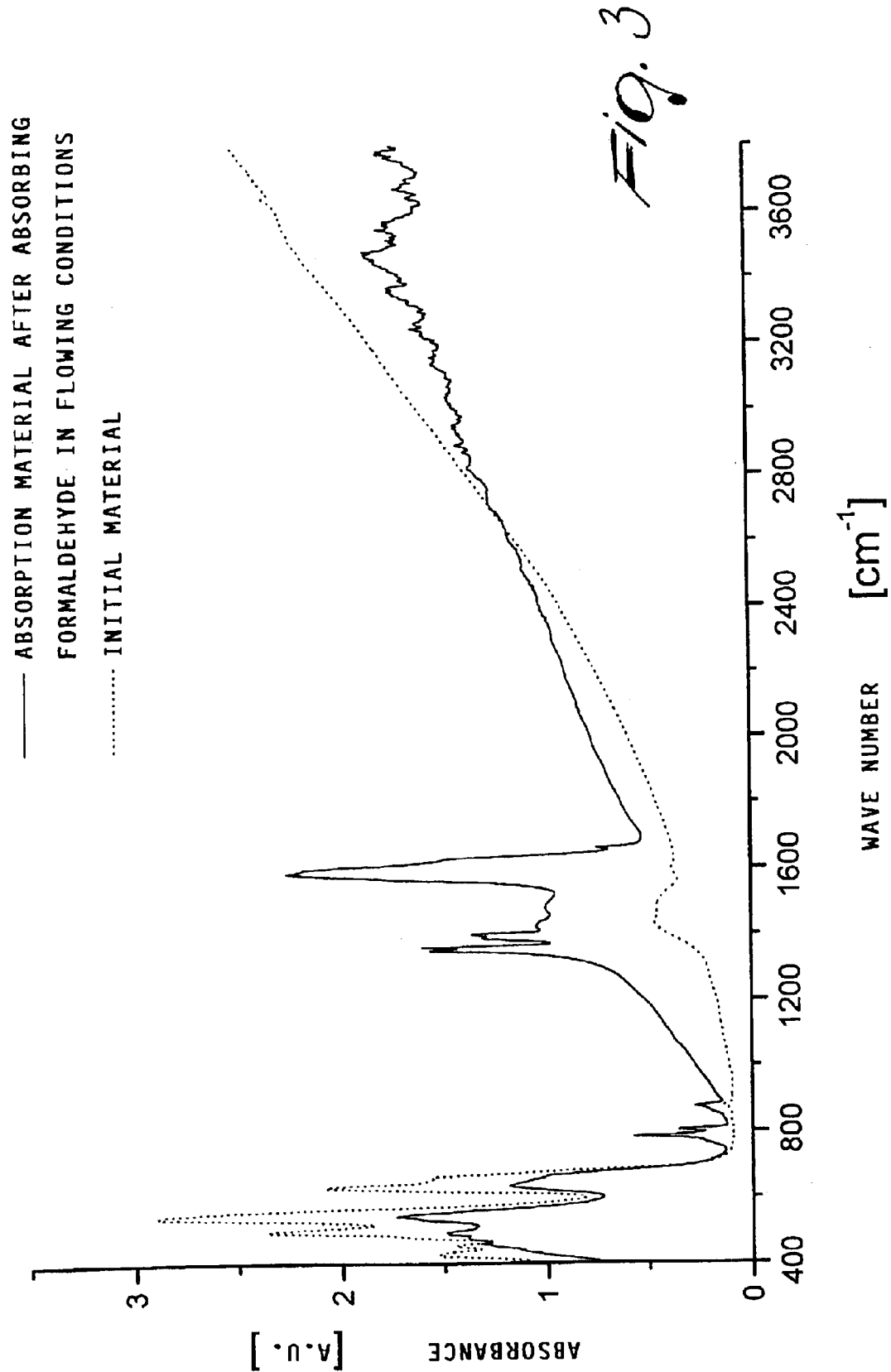
FIG. 3 is an IR spectrum of absorption material after absorbing formaldehyde in flowing conditions and IR spectrum of initial material.

At the end of the experiment, the absorption material showed an increase in weight ($\Delta W$) of 18.3%, which corresponds to a weight variation of 199 mg of the absorption material. The fact that the weight increase is actually due to the incorporation of $H_2CO$ was verified by subjecting to solid-state IR spectroscopy the absorption compound after contact with the gaseous mixture. Solid-state IR spectroscopy always showed the presence of formate, carbonate groups and modest quantities of hydrated phases in the materials discharged from the reactor (FIG. 3).

At the end of the absorption experiment, the water contained in the first trap was analyzed and showed that negligible amounts of formaldehyde (approximately 3 mg in the experimental conditions used) were present, while formaldehyde was absent in the second trap. Formaldehyde was detected spectrophotometrically according to the acetyl acetone method cited in the UNI EN 717-3 standard for formaldehyde determination. The determination is based on the Hantzsch reaction, in which the formaldehyde in aqueous solution reacts with acetyl acetone and ammonium ions, releasing diacetyl dihydrolutidine (DDL). DDL has an absorption maximum at 412 nm. The reaction is specific of formaldehyde.

The numeric values of $\Delta W$ are given only a semiquantitative meaning, since the extent of the absorption in isothermal conditions is regulated by the kinetics of the system, which also depends on the status, the extension of the surface of the materials, and the degree of hydration of the products formed in the absorption method. However, based on the low quantity of formaldehyde found in the trap, one deduces that the material absorbs formaldehyde easily and almost totally.

A.2 Experiments of absorption in a closed environment

Experiments of absorption in a closed environment were conducted at ambient temperature, by using ~0.5 g of $Ca_{4.1}Cu_5O_{10}$ absorption material in powder form as obtained from synthesis, without further modifications. The duration of the experiments was 3, 8 and 30 days.

Figure 4B:
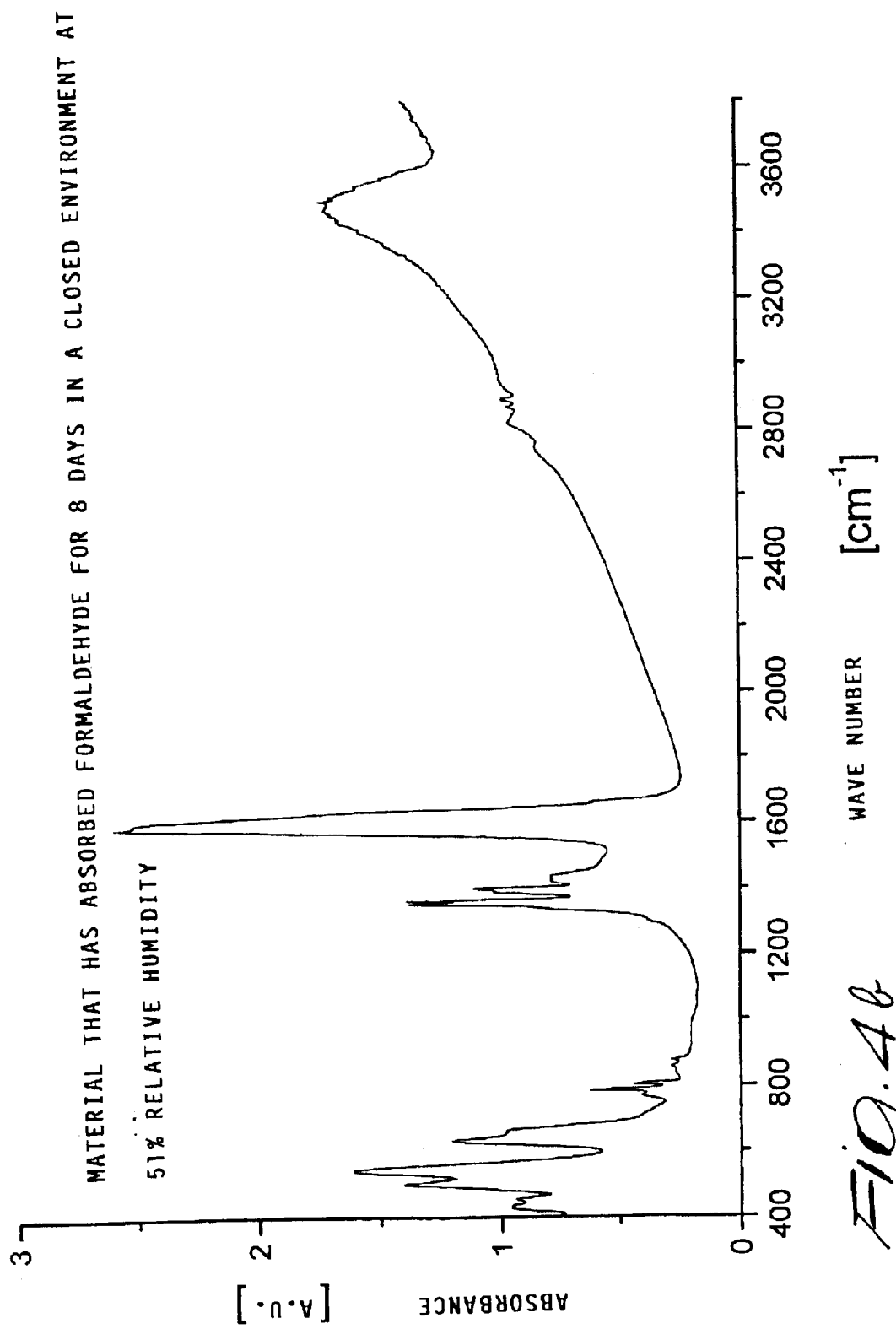
FIG. 4 is an IR spectra of absorption material after absorbing formaldehyde in closed ambient at different relative humidity: a) 100% relative humidity fro 8 days; b) 51% relative humidity for 8 days; c) 75% relative humidity for 30 days.

An increase in weight of the absorption material occurred in all the experiments. The weight variation increases as the duration of the experiment increases and as the relative humidity of the atmosphere used in the experiment increases. For experiments lasting 8 days, a weight increase of 17% and 84% was observed for relative humidities of 51 and 100%, respectively. After 30 days of contact with the indicated gaseous mixture at a relative humidity of 75%, the observed weight increase of the material was 57%. As mentioned, the numeric values of $\Delta W$ are given only a semiquantitative meaning. The samples recovered after the absorption method show a morphological change that indicates the forming of copper formate during the absorption method (the material assumes a pale blue-green color). The presence of formate, carbonate and hydrated phases was verified by IR spectroscopy. FIGS. 4a, 4b and 4c plot the IR spectra for the three relative humidities respectively for 8 days (a, b) and 30 days (c).

B. Regeneration of the $Ca_{4.1}Cu_5O_{10}$ absorption material

The absorption material used in the absorption methods was subjected to a thermal treatment at various temperatures and in an atmosphere of synthetic air.

In particular, for treatments up to 200° C. the material remained unchanged, as verified by IR spectroscopy.

For treatments at temperatures 200° C. <T<700° C., the formate oxidized to carbonate and copper oxide appeared.

Figure 5:
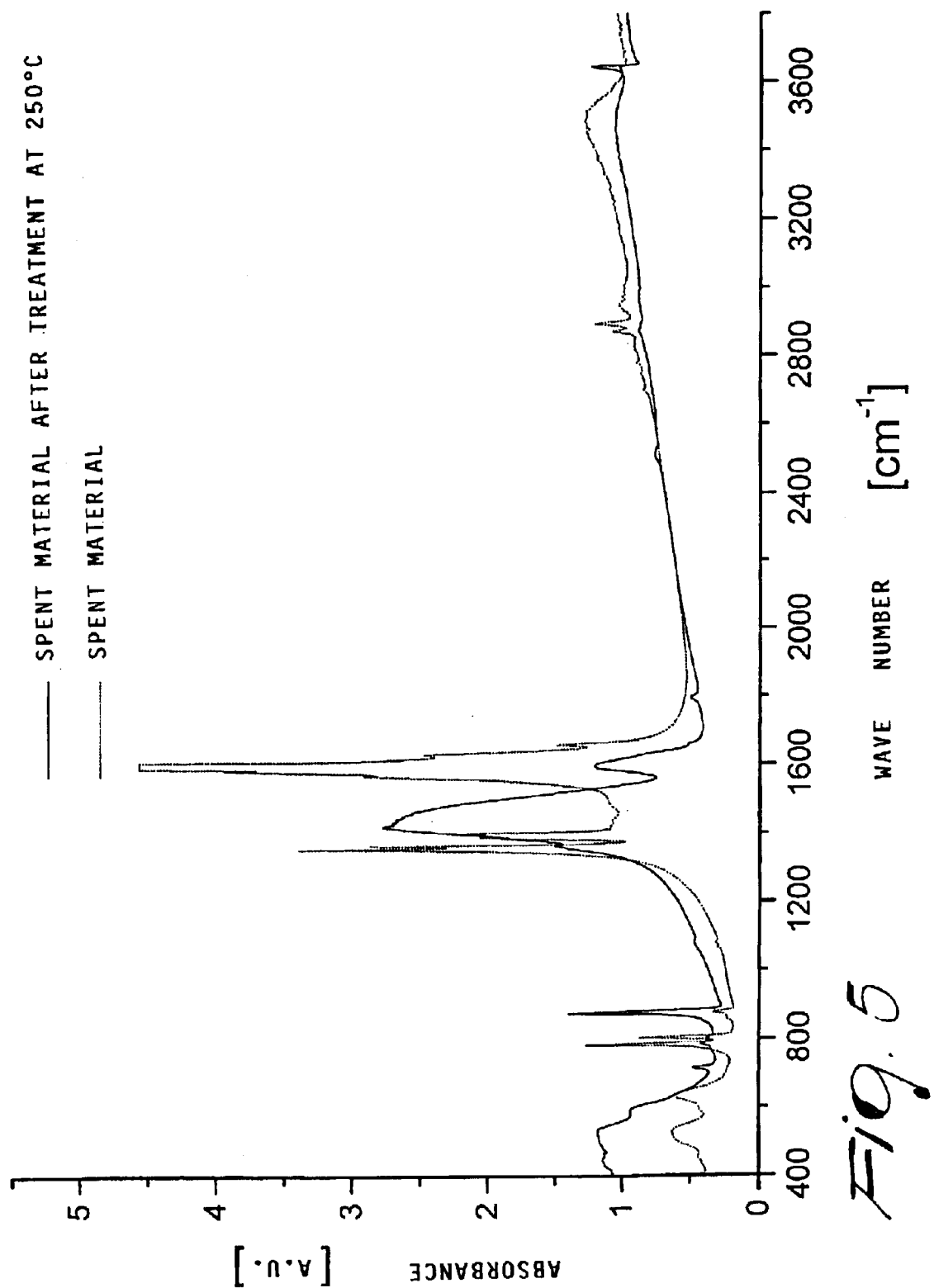
FIG. 5 is an IR spectrum of spent material after treatment at 250° C.

For example, the material recovered from the absorption method was converted at 250° C. into the mixture of reagents used in the synthesis of $Ca_{4.1}Cu_5O_{10}$ as shown by the IR spectra of FIG. 5.

Figure 6:
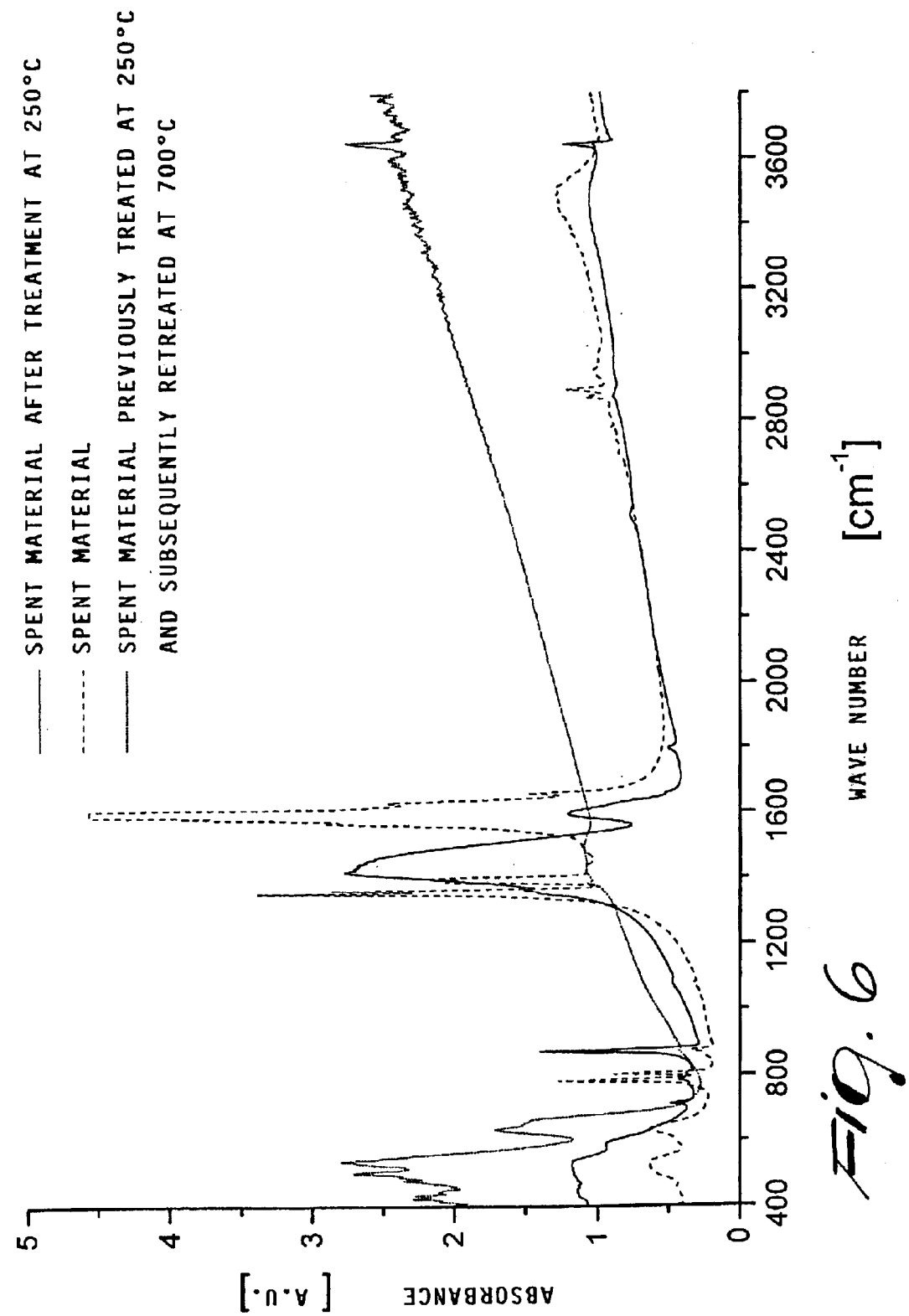
FIG. 6 is an IR spectrum of spent material, IR spectrum of spent material after treatment at 250° C., and IR spectrum of spent material previously treated at 250° C.

Regeneration of the $Ca_{4.1}Cu_5O_{10}$ absorption material can be performed by treating the mixture of carbonates and oxides obtained in a stream of oxygen at 700° C., as shown in FIG. 6.

Figure 7A:
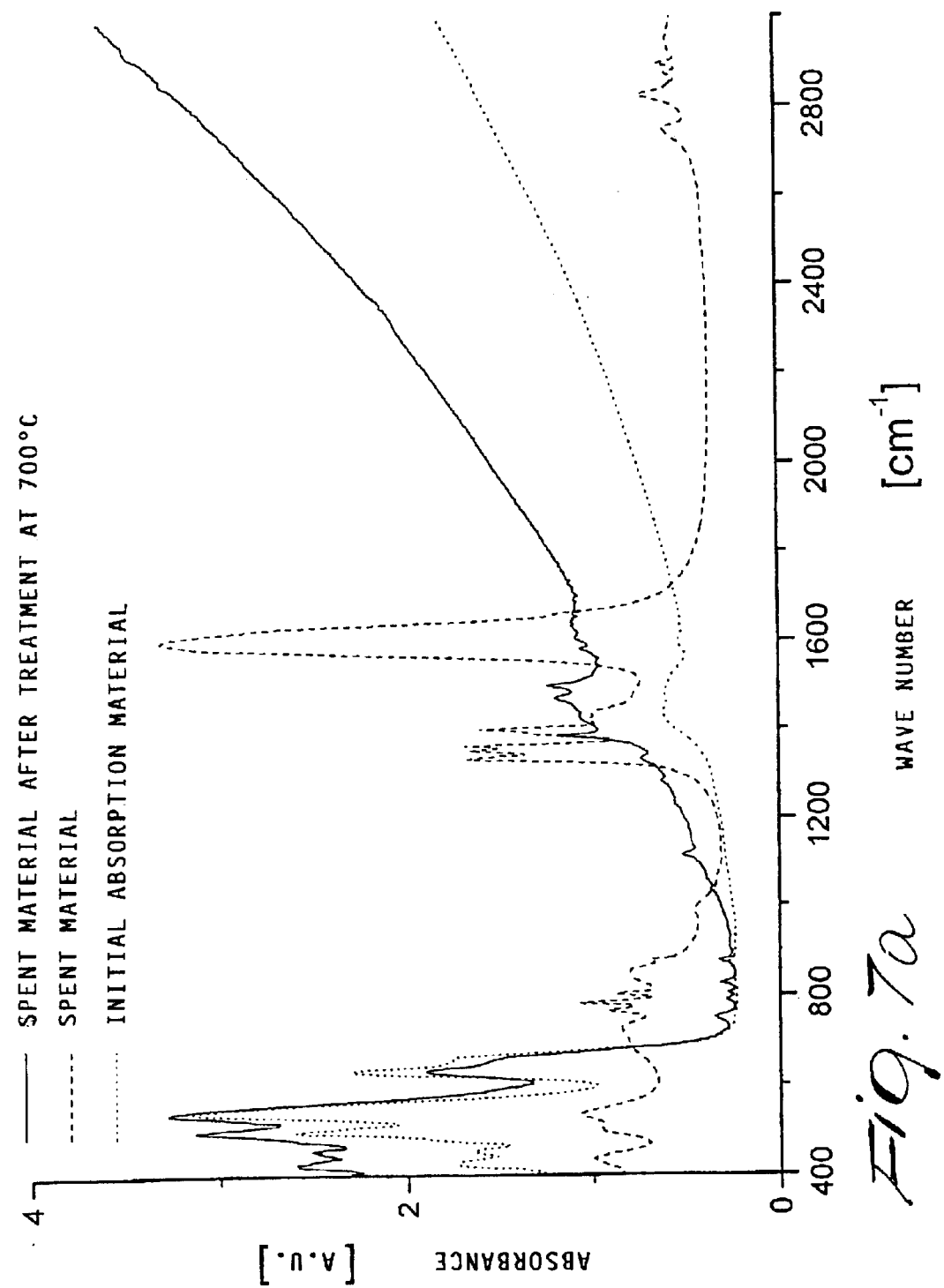
FIG. 7a is an IR spectrum of the powders of the initial absorption material and IR spectrum of the material regenerated by treatment at 700° C.
Figure 7B:
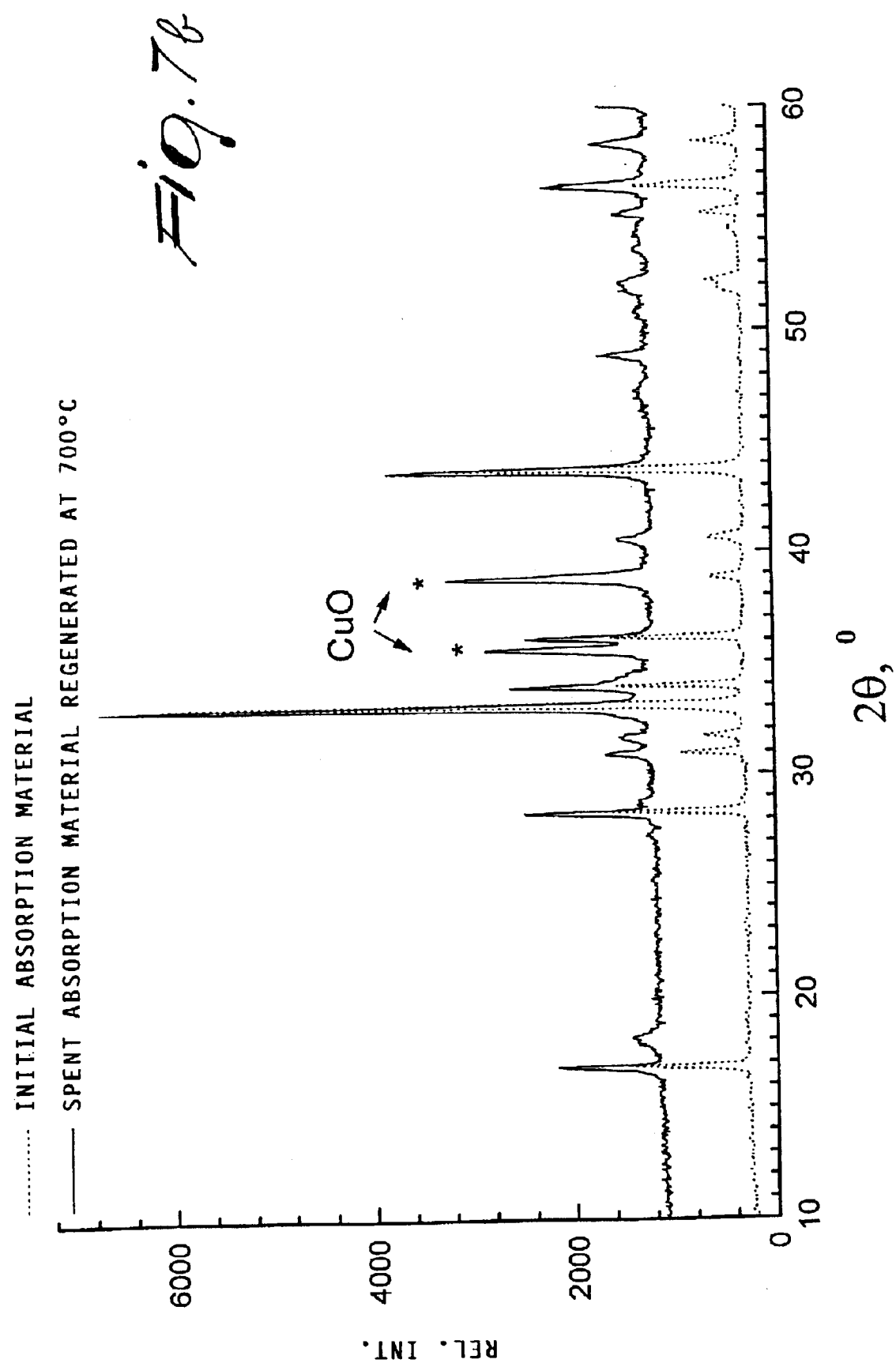
FIG. 7b is an X-ray diffraction spectrum of the powders of the initial absorption material and X-ray diffraction spectrum of the material regenerated by treatment at 700° C.

The results of the experiments shown in FIGS. 7a and 7b bear witness to the fact that the absorption material has been regenerated also as a consequence of the heating to 700° C. in a stream of oxygen of the material recovered from the absorption experiments without pretreatment at a lower temperature, for example at 250° C.

FIG. 7a plots the IR spectrum, and FIG. 7b plots the X-ray diffraction spectrum of the powders of the material regenerated by treatment at approximately 700° C.

The measurements made with the IR spectroscopy technique have proved that the product of the absorption of $H_2CO$ on the part of the compound according to the invention is $HC(O)O^-$, in the form of copper formate. Accordingly, without intending to be constrained by a particular mechanism, one can consider that the following reaction of absorption at ambient temperature and in the presence of formaldehyde, oxygen and water occurs:

1)

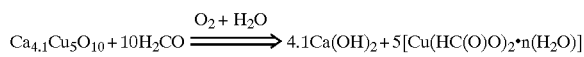

One can consider that the reaction, by treatment of the product of 1) at 250° C., follows the conversion method

2)

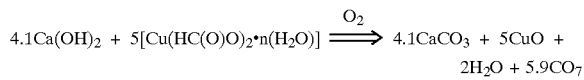

The regeneration method at 700° C. of the product 2) follows the following synthesis reaction:

3)

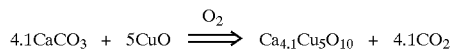

Therefore the absorption material, in the presence of oxygen and humidity, is capable of absorbing formaldehyde in the form of formate and of oxidizing it to carbonate. The products of the reaction of absorption-oxidation of the formaldehyde on the part of $Ca_{4+x}Cu_5O_{10}$ ($0 \leq x \leq 1$) and their derivatives by isovalent and heterovalent substitutions, particularly $Ca_{4.1}Cu_5O_{10}$, can be converted back to the initial absorption material with elimination of $CO_2$ and $H_2O$.

It is worth noting that the formaldehyde absorbed by virtue of the method according to the present invention is not only removed from the environment but is completely converted into products that are fully environmentally compatible.

The cost of the compound used as absorber in the present invention is particularly low owing of the abundance of its components and the simplicity of its synthesis.

It is believed that the method according to the present invention, which uses a material capable of absorbing formaldehyde and allows to convert formaldehyde into water and carbon dioxide, distinguishes itself fully from the methods proposed so far within the scope of the solution of the problems linked to the release of formaldehyde.

As is evident to the reader, various modifications, adaptations and variations of the above specific description can be performed without abandoning the teaching of the present invention.

What is claimed is:

1. A method for absorbing formaldehyde from gaseous mixtures that contain it, comprising the step of contacting gaseous mixtures that contain formaldehyde with absorption compounds constituted by mixed oxides of copper chosen among $Ca_{4+x}Cu_5O_{10}$, where $0 \leq x \geq 1$, derivatives thereof by isovalent and/or heterovalent substitutions, and mixtures thereof.

2. The method according to claim 1, wherein said absorption compound is $Ca_{4+1}Cu_5O_{10}$, where $0 \leq x \geq 1$.

3. The method according to claim 2, wherein said absorption compound is $Ca_{4.1}Cu_5O_{10}$.

4. The method according to claim 1, wherein said absorption compound is a derivative by isovalent and/or heterovalent substitution of the $Ca_{4+x}Cu_5O_{10}$ compound, where $0 \leq x \geq 1$.

5. The method according to claim 4, wherein said absorption compound is a derivative of $Ca_{4+x}Cu_5O_{10}$, where $0 \leq x \geq 1$, by substitution on the sites occupied by Ca.

6. The method according to claim 5, wherein the absorption compound is chosen from the group constituted by $Ca_{0.85}Mg_{0.15}CuO_2$ and $Ca_{0.85}Sr_{0.15}CuO_2$.

7. The method according to claim 4, wherein said absorption compound is a derivative of $Ca_{4+x}Cu_5O_{10}$, where $0 \leq x \geq 1$, by isovalent and/or heterovalent substitution on the sites occupied by Cu.

8. The method according to claim 7, wherein said derivative is $CaCu_{0.45}Ni_{0.15}O_2$.

9. The method according to claim 1, wherein absorption occurs in the presence of oxygen.

10. The method according to claim 1, wherein absorption occurs in the presence of water vapor.

11. The method according to claim 2, wherein absorption occurs at a temperature in the range between 0 and 150° C.

12. The method according to claim 2, wherein absorption occurs at ambient temperature.

13. The method according to claim 1, wherein said step of contacting said gaseous mixtures containing formaldehyde with absorption compounds is followed by a step of treatment at temperatures above 200° C. of the absorption compounds for converting the formaldehyde into carbon dioxide and water.

14. The method according to claim 1, further comprising a step for treating the absorption compounds at a temperature of approximately 700° C. to regenerate said absorption compounds.

15. The method according to claim 5 wherein the substitution on the sites occupied by Ca is with an element selected from the group consisting of Mg and Sr.

* * * * *